United States Patent
Koertge

[19]

[11] Patent Number: 5,878,112

[45] Date of Patent: Mar. 2, 1999

[54] MEDICAL SYSTEM HAVING MOVABLE COMPONENTS AND A CONTROL DEVICE FOR PREVENTING COMPONENT COLLISIONS

[75] Inventor: Detlef Koertge, Nuremberg, Germany

[73] Assignee: Siemens Aktiengesellschaft, Munich, Germany

[21] Appl. No.: 881,350

[22] Filed: Jun. 24, 1997

[30] Foreign Application Priority Data

Jun. 25, 1996 [DE] Germany ................ 196 25 409.4

[51] Int. Cl.$^6$ ............................................. A61B 6/04
[52] U.S. Cl. ................................... 378/209; 378/8
[58] Field of Search .................... 378/8, 95, 209; 600/407, 408, 415

[56] References Cited

U.S. PATENT DOCUMENTS 4,969,170 11/1990 Kikuchi et al. ............... 378/91
5,323,470 6/1994 Kaara et al. .................. 382/1

FOREIGN PATENT DOCUMENTS 3604955 8/1987 Germany .
4335301 12/1994 Germany .

*Primary Examiner*—Don Wong
*Assistant Examiner*—David Vernon Bruce
*Attorney, Agent, or Firm*—Sughrue, Mion, Zinn, Macpeak & Seas, PLLC

[57] ABSTRACT

A medical system, such as an X-ray diagnostic device, having adjustable components, including a patient table, and having a monitoring device for determining the relative positions of the components and preventing collisions between them. Signals indicating the positions, the directions of motion and the speeds of movement of the components are fed directly from the drives and sensors of the components to the monitoring device. Calculations for controlling the components are carried out by a neural network, which has been appropriately trained in a learning phase.

5 Claims, 1 Drawing Sheet

MEDICAL SYSTEM HAVING MOVABLE COMPONENTS AND A CONTROL DEVICE FOR PREVENTING COMPONENT COLLISIONS

The following disclosure is based on German Patent Application No. 19625409.4, filed on Jun. 25, 1996, which is incorporated into this application by reference.

FIELD OF AND BACKGROUND OF THE INVENTION

The invention relates to new and useful improvements in medical systems. More particularly, the invention relates to medical systems, such as X-ray diagnostic devices, having various adjustable components including a patient table and having a control device for determining the position of the components and preventing collisions between them.

In the case of such medical devices, there is a risk that the adjustable components, which can move with several degrees of freedom, will collide with one another. For instance, in the X-ray diagnostic devices mentioned, the image generation system may carry a C-shaped bracket which can be adjusted along its circumference in a mount and which holds the X-ray source and the radiation receiver at its ends. This bracket or the components mounted thereon may inadvertently collide, for example, with the patient table. This risk is all the greater since the operating personnel are often reoccupied with observing the system's screens or with other operations and can therefore concentrate only peripherally on monitoring the movable components.

Various methods are known for avoiding collisions between the C-bracket of an X-ray device and the table or the patient. One such method, a calculating method, is based on a wire model or volume model of the X-ray system. With the aid of the model, the planes of intersection of objects capable of mutually touching can be calculated in a computer. One disadvantage of this method is that a collision is detected only when parts of the system actually touch. Since, however, the drives need a certain distance in order to come to a standstill, the instant of contact is generally already too late. In order to solve this problem, the model can be enlarged by a specific percentage, so that a virtual instant of contact is determined before the actual collision, and hence timely braking is possible. However, in practice it would be desirable for the speed of movement to be reduced already in the case of an approach or in the case of a detectable risk of collision, in order to enable oscillation-free braking of the system. A further problem in the implementation by means of volume modelling, as taught e.g. by German Patent DE 36 04 955 C2, is the enormous computing effort associated with the complex geometric shapes encountered, for example, in an X-ray system.

A quite different method for avoiding collisions is described in German Patent DE 43 35 301 C1. Instead of detecting the position of the components by means of transmitters on the components or the adjusting motors, as in DE 36 04 955 C2, two cameras and a three-dimensional neural network are provided. These observe the movements of the components and intervene appropriately in the case of a risk of collision. One doubtless advantage of such a monitoring device using a three-dimensional neural network is that collisions with movable objects or persons in the examination room can also be detected. However, an associated disadvantage is that the image recording operation is subject to disturbance both by the personnel moving around within the examining room and also by the surfaces of the objects being observed. Although this disadvantage could certainly be circumvented by fitting the system with further cameras, this would further increase the complexity of the system. Even with two cameras, in order to calculate the image data and to reconstruct the objects in the computer, complicated image processing algorithms and appropriately fast computers are necessary, which makes the system very expensive. Accordingly, for the vast majority of applications, the added complexity and expense of this latter method outweighs the associated advantages.

OBJECTS OF THE INVENTION

A first object of the invention is therefore based on a need in the art for a medical system with an improved device for preventing the collision of adjustable system components. In particular, there is a need for such a medical system having a considerably reduced outlay in terms of equipment and especially computer power, and hence expense. It is a further object of the invention to provide a system capable of effectively preventing mutual collisions between the adjustable components of the system. Yet another object is providing a system of this type, in which the movement of the components is appropriately slowed in the event of an approach, and in which the components can be brought to a standstill in an oscillation-free manner just prior to contact.

SUMMARY OF THE INVENTION

These and other objects are achieved in accordance with a medical system that includes a plurality of adjustable components, one of which is a patient table. A plurality of drives and sensors are respectively connected to these adjustable components. A control device, connected to the drives and sensors, determines position information relating to the adjustable components by gathering data of respective positions, respective directions of motion and respective speeds of movement of the components. These data are gathered directly from the drives and sensors of said components and are processed by a neural network internal to the control device, after the neural network has been trained in a learning phase. The results of the processing carried out by the neural network are then used to control the components and thereby prevent collisions between the respective components. Particularly advantageous refinements of the invention are the subject matter of the dependent claims.

In accordance with the invention, the positions, the directions of motion and the speeds of movement of the components are picked up directly from the drives and sensors of the components. The calculations for controlling the components are then carried out via a neural network, which has been appropriately trained in a learning phase.

One advantage associated with the invention is that the information about the position and current direction of motion or speed of movement of each system component is obtained directly from the drives and sensors of the component. As a result, the entire image chain of the monitoring and collision preventing device according to German Patent DE 43 35 301 C1 is dispensed with, which leads to an enormous simplification and reduction in costs.

On the other hand, the calculations are carried out by a neural network, which has been appropriately trained in a learning phase, and, accordingly, the invention benefits from neural network processing. In this regard, it should be noted that it is unimportant to the invention whether only one or whether several drives are active at the same time, since a neural network processes all the input variables in parallel, in evaluating the movement.

Moreover, because the input of the data is not carried out using cameras, the problems associated with cameras, such as concealment or shadowing by nearby objects and persons, are avoided. Also, since the neural network supplies continuous output data as a function of the input variables, it is possible not only to detect actual collisions but also to recognize components approaching one another.

As indicated above, the neural network of the present invention, in actual operation, evaluates only information acquired and derived from the sensors and drives, to assess the position, current direction of motion and/or speed of movement of the system components. By limiting the information evaluated to that derived from the sensors, drives, etc., the invention not only avoids the necessity of a very complex image evaluation system, which would otherwise have to be connected upstream of the neural network, as in DE 43 35 301 C1, but also permits the use of a very much simpler neural network.

By arranging the inventive medical system in the manner described, direct monitoring of collisions with the patient, as practiced, for instance, by German Patent DE 43 35 301 C1, is omitted from the neural network processing. Neither an envelope curve for the patient is prescribed nor are the outlines of the patient automatically detected via an image monitoring system. However, as a practical matter, dispensing with this feature not only results in great savings in outlay and cost but also has relatively little practical significance. One reason for this is that mutual collisions between components, which often result in considerable damage, are substantially more probable than collisions with the patient. Also, other, relatively cost-effective safety measures can be provided to ensure that components of the medical system, e.g., some part of an image acquisition system of an X-ray diagnostic device, are prevented from colliding with the patient. Thus, collision avoidance means, such as simple contact feelers provided on the front of the image components, are a reliable and unproblematical means of ensuring the patient's safety against injury.

According to one refinement of the invention, the neural network is preferably a single layer radial base function network (RBF network).

The input layer of such a single layer RBF network pre-processes the input data in such a manner that they can then be processed in the network layer by the layer of RBF neurons. In the output layer, the resulting data are put into a form in which they can then be used by the other elements of the medical system.

Use of an RBF network enables the medical system to interpolate output data between points, where no learning values exist. With regard to the present invention, this is a particularly important property of an RBF network. Because of the safety requirements which have been established for such systems, collisions must also be avoided at those points which were not taken into account explicitly in the learning phase. Other network topologies do not exhibit these advantageous properties.

Moreover, the inventive neural network may be configured to learn from potential collisions occurring during actual operation of the medical system. This could result, e.g., in response to activation of the previously mentioned collision avoidance means. This highlights a further advantage of radial base functions: even if new learning steps are carried out, the network does not forget the old learning results.

BRIEF DESCRIPTION OF THE DRAWINGS

The invention, along with further advantages, features and details, is further described with reference to a preferred embodiment described below and illustrated in drawing FIG. 1, which shows an X-ray diagnostic device in schematic form, as one example of a medical system according to the invention.

DETAILED DESCRIPTION OF THE PREFERRED EMBODIMENTS

Figure 1:
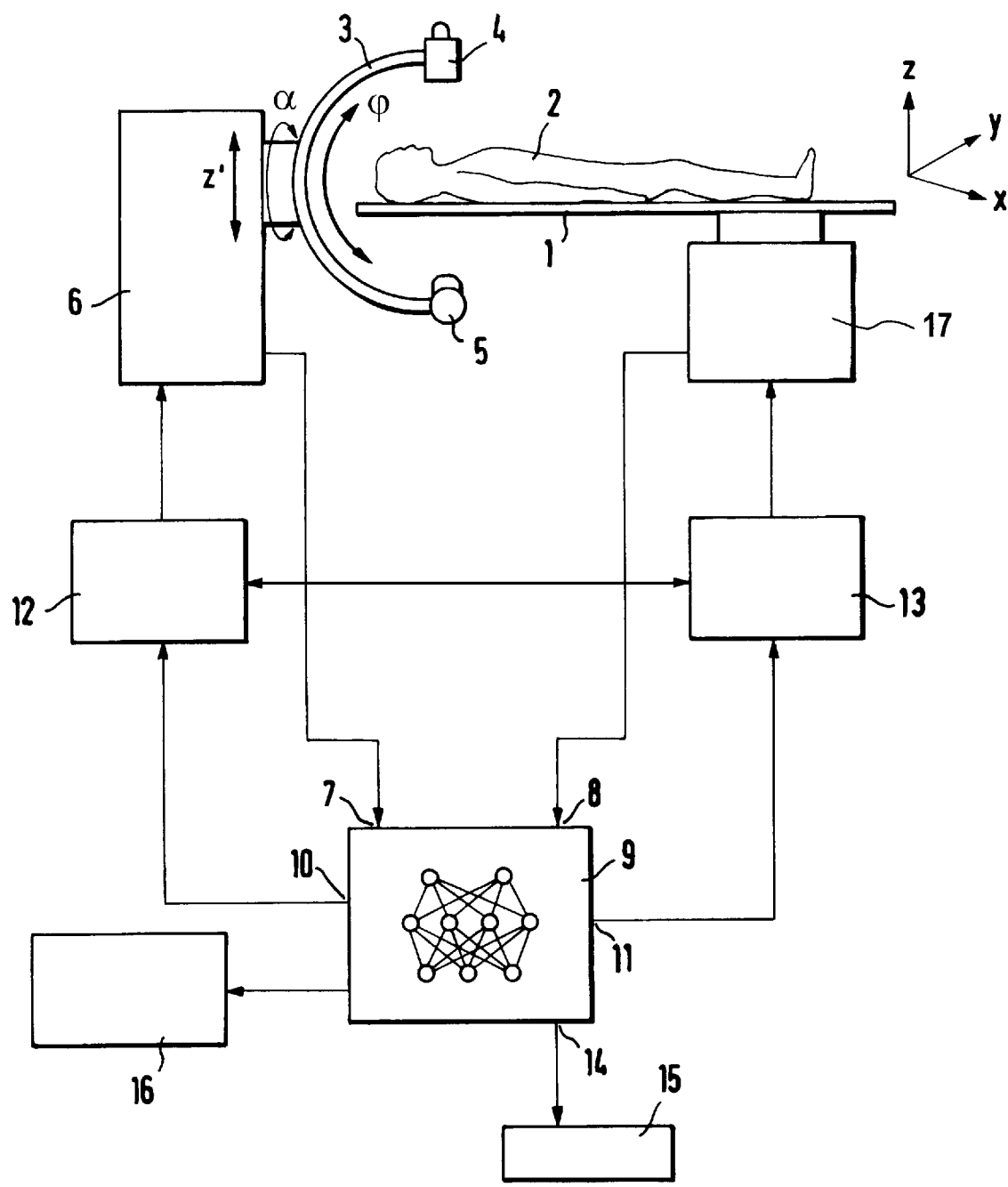

The X-ray diagnostic device shown in FIG. 1 includes a number of adjustable components, including an adjustable table 1 for the patient 2, a C-bracket 3 supporting an X-ray source 5 on one end and a radiation receiver 4 on the other, a stand 6 containing the drives for actuating the C-bracket, and a stand 17 for the patent table 1. Each of these components is capable of performing one or more separate adjustment motions. For instance, the C-bracket device is preferably adjustable with regard to an angle of axial rotation $\alpha$, an orbital position $\emptyset$ of the X-ray source 5 and the receiver 4, a position of the radiation receiver 4, as well as a height z' of the C-bracket 3. The X-ray diagnostic device is outfitted in such a manner that information regarding the various motion parameters for the movable components is either acquired directly from the adjusting motors themselves or from sensors (not shown) fitted to the components.

The combined information is fed as position data to one of the inputs 7, 8 of a control device 9 containing an RBF neural network. After the learning phase, this RBF network supplies control signals at the outputs 10, 11 for the drives of the components. In the exemplary embodiment shown in FIG. 1, these drives include a drive 12 for the actual X-ray device and a drive 13 for the patient table 1. It should be noted that, while FIG. 1 illustrates these control signal outputs merely in schematic form, in actual fact each of these drives is composed of several independent and/or interdependent drives. Accordingly, the signal output from the control device 9 to, e.g., the drive 12, will include several different types of control signals, in order to adjust, e.g., the height z' of the C-bracket, or its angle, or the orbital position independently of one another.

The RBF network can additionally be configured to output a warning signal via an output 14, in order to activate an acoustic and/or optical warning device 15 as soon as a collision threatens. This added feature is useful, since the attention of the operator during an examination is not directed to possible collision points but rather to the subject matter of the examination. Supplementing the functionality of the control device 9 itself with the warning indicator provides a back-up for the examiner that is both practical and cost-effective.

As discussed above, the neural network is configured to cause reductions in the speed of the movement of the components when potential collisions are detected. This allows the movable components to be brought to a standstill gradually, without experiencing the oscillations associated with abrupt stops. Thus, in the event of an approach, the neural network will not completely and abruptly prevent movement but rather will reduce the speed appropriately. According to one refinement, a region of probable collisions can to be determined by the neural network, which region can then be calculated more precisely through conventional methods. The additional calculations can be performed, e.g., with the aid of a standard collision computer 16, as illustrated in the drawing.

The above description of the preferred embodiments has been given by way of example. From the disclosure given, those skilled in the art will not only understand the present invention and its attendant advantages, but will also find apparent various changes and modifications to the structures disclosed. It is sought, therefore, to cover all such changes and modifications as fall within the spirit and scope of the invention, as defined by the appended claims, and equivalents thereof.

What is claimed is:

1. A medical system comprising:

a plurality of adjustable components, including a table for supporting a patient;

a plurality of drives and sensors respectively connected to said adjustable components; and a control device, connected to said drives and sensors, for determining respective positions of said components and preventing collisions between said respective components, said control device comprising a neural network, wherein said control device gathers data for respective positions, respective directions of motion and respective speeds of movement of said components directly from said plurality of drives and sensors of said components, and wherein said neural network carries out processing for controlling said components in accordance with the gathered data, following training of said neural network in a learning phase.

2. The medical system according to claim 1, wherein said neural network is a single layer radial base function network.

3. The medical system according to claim 1, wherein the medical system is an X-ray diagnostic device, and said plurality of adjustable components comprises said patient table and a C-bracket supporting a radiation source and a radiation receiver.

4. The medical system according to claim 1, wherein said neural network outputs data for controlling said components, in accordance with the processing of the gathered data, continually during operation of said control device.

5. A method for preventing component collisions in a medical system, the components being movable, relative to other system components and structures, in at least one degree of freedom in accordance with respective drive signals output by respective component drive sources, comprising:

outputting positional information, including at least one of location information, direction information, and speed information, for each degree of freedom of each movable component, the positional information being output from signal outputs connected either to the respective component drive sources or to the components;

supplying the positional information as input variables directly from the signal outputs to a neural network previously trained in a learning phase;

processing the input variables in the neural network, for determining positions of the respective components and generating control signals; and outputting the control signals to the respective component drive sources for preventing component collisions in the medical system.

* * * * *